United States Patent [19]

Crast, Jr.

[11] Patent Number: 4,694,079

[45] Date of Patent: Sep. 15, 1987

[54] 3-PROPENYL CEPHALOSPORIN SOLVATES

[75] Inventor: Leonard B. Crast, Jr., North Syracuse, N.Y.

[73] Assignee: Bristol-Myers Company, New York, N.Y.

[21] Appl. No.: 759,805

[22] Filed: Jul. 29, 1985

[51] Int. Cl.$^4$ ................. C07D 501/22; A61K 31/545
[52] U.S. Cl. ..................................... 540/215; 540/219
[58] Field of Search .................... 544/22, 25; 540/215

[56] References Cited

U.S. PATENT DOCUMENTS 3,985,741 10/1976 Crast, Jr. et al. ............... 260/243 C
4,520,022 5/1985 Hoshi et al. ......................... 514/200
4,525,587 6/1985 Chou et al. ........................... 544/25

Primary Examiner—Nicholas S. Rizzo
Attorney, Agent, or Firm—Robert E. Carnahan

[57] ABSTRACT

7-[(D)-2-Amino-2-(4-hydroxyphenyl)acetamido]-3-[(Z)-1-propenyl]ceph-3-em-4-carboxylic acid in the form of its crystalline dimethylformamide solvate (1/1.5) has been provided.

4 Claims, 1 Drawing Figure

3-PROPENYL CEPHALOSPORIN SOLVATES

FIELD OF THE INVENTION

The invention relates to certain solvates of a specific cephalosporin antibiotic (Class 544 Subclass 16).

BACKGROUND OF THE INVENTION

7-[(D)-2-Amino-2-(4-hydroxyphenyl)acetamido]-3-[(Z)-1-propenyl]ceph-3-em-4-carboxylic acid, sometimes referred to as BMY-28100, is an orally effective cephalosporin antibiotic having a broad spectrum of antibacterial activity against both Gram positive and Gram negative organisms. It is the subject of U.S. Pat. No. 4,520,022 patented May 28, 1985.

SUMMARY OF THE INVENTION

In the synthesis of organic compounds, and of cephalosporin antibiotics in particular, by multi step processes it is usually desirable to develop a process in which one or more of the intermediates is a stable crystalline compound. The reason for this is that crystalline compounds are ordinarily obtainable in a high state of purity, and, when stable under storage conditions, can be used to accumulate inventories of intermediates during manufacturing campaigns. The present invention provides such a storage stable crystalline intermediate in the form of the dimethylformamide solvate of BMY-28100. This solvate has a characteristic crystalline structure containing BMY-28100 and dimethylformamide in the molecular ratio of 1 to 1.5. The crystalline structure has been characterized by measurement of the X-ray powder diffraction pattern which is described hereinafter. It has been further characterized by its infrared absorption spectrum measured on the solid material when pelletized with potassium bromide, and as to composition by its nuclear magnetic resonance spectrum.

DETAILED DESCRIPTION OF THE INVENTION

Figure 1:
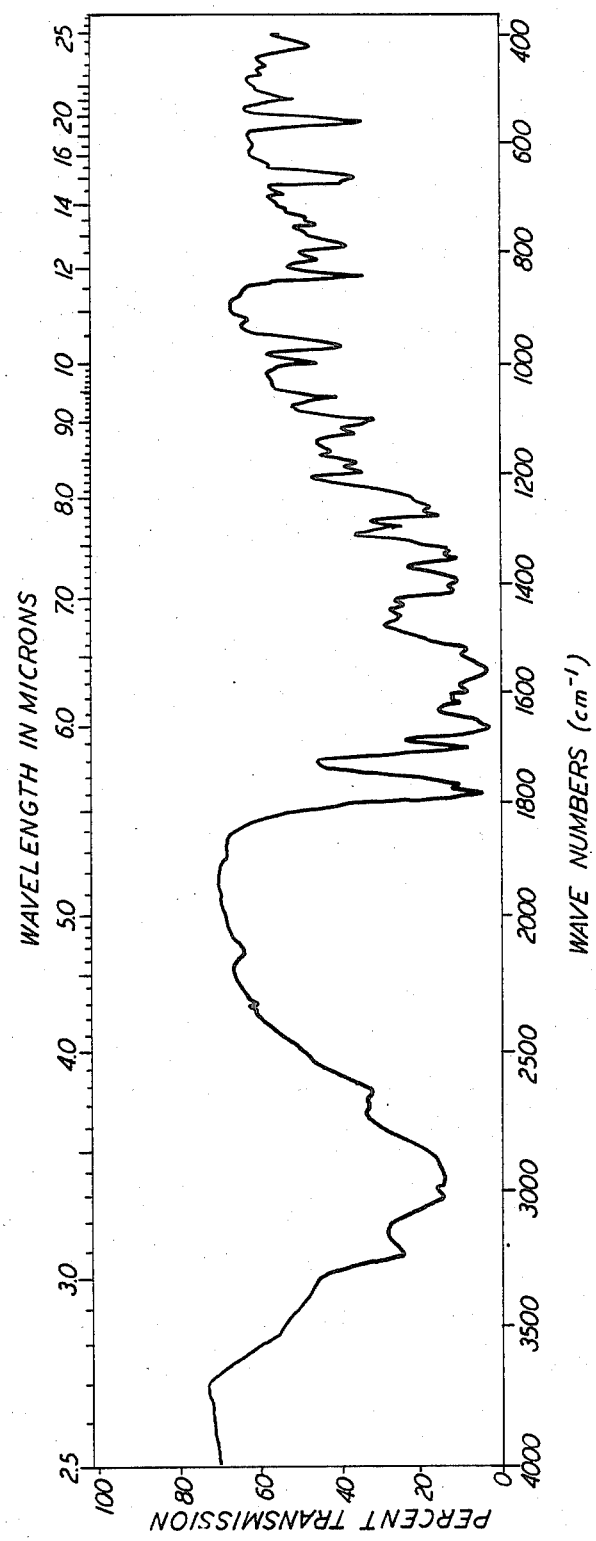
FIG. 1 is a tracing of the infrared absorption spectrum of the 1.5 dimethylformamide solvate of BMY-28100.

The dimethylformamide solvate is preferably formed by contact of BMY-28100 in its neutral or zwitterionic form in solution with dimethylformamide. A solvent is selected which is inert and non-reactive with either the BMY-28100 or the dimethylformamide and in which the desired solvate is insoluble. Suitable solvents include dimethylformamide, methanol, and mixtures thereof with water. Aqueous dimethylformamide is the preferred reaction medium. At least 1.5 molecular proportions of dimethylformamide per mole of BMY-28100 is used. The pH is adjusted to within the range of about 4.5 to 6.0, preferably with a tertiary aliphatic amine such as triethylamine. A substantial excess of dimethylformamide is preferably employed. A volume of dimethylformamide equal to about twice the volume of aqueous solution of BMY-28100 is suitable. A higher water soluble alkanol (2 to 4 carbon atoms) such as isopropanol may be added to the mixture to enhance the efficiency of crystallization.

The so produced 1.5 dimethylformamide solvate is readily collected by filtration and can be washed on the filter with non-solvents such as dimethylformamide, acetone, or methylene chloride and is storage stable in ordinary containers for prolonged periods. No decomposition is evident on exposure to extremes of storage temperature or humidity.

The BMY-28100 neutral or zwitterionic form may be recovered from the DMF solvate by dissolution thereof in water and recovery of the BMY-28100 from the aqueous solution for instance by lyophilization. Dimethylformamide solvates of other cephalosporin antibiotics have been described in the art as intermediates useful for isolation, purification, and storage purposes. For instance U.S. Pat. No. 3,985,741 patented Oct. 12, 1976 is concerned with the dimethylformamide solvate of cefadroxil, and U.S. Pat. No. 4,525,587 patented June 25, 1985 refers to the dimethylacetamide solvate of ceftazidime.

DESCRIPTION OF SPECIFIC EMBODIMENTS

The following abbreviations are used.
DPM=diphenylmethyl,
Ph=phenyl,
BOC=COOC(CH$_3$)$_3$,
DCC=dicyclohexylcarbodiimide,
TFA=trifluoroacetic acid,
EtOAc=ethyl acetate,
DMF=dimethylformamide,
TSP=trimethylsilylpropanesulfonic acid,
28100=7-[(D)-2-amino-2-(4-hydroxyphenyl-)acetamido]-3-[(Z)-1-propenyl]ceph-3-em-4-carboxylic acid.

PROCEDURE 1

Diphenylmethyl 7-Phenylacetamido-3-((Z)-propen-1-yl)ceph-3-em-4-carboxylate

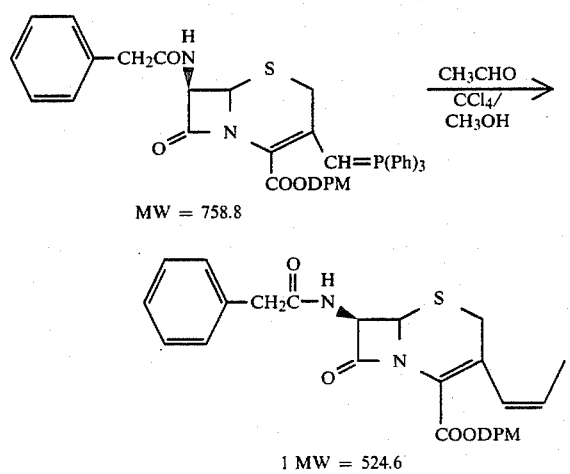

A stirred solution of 18 l of CCl$_4$, 1.8 l methanol and 12 g p-benzoyl benzoic acid was cooled to 8° C. 970 ml of acetaldehyde were added. The temperature of the resulting solution rose to +14° C. After five minutes, 588 g (0.7749 mole) of diphenylmethyl 7-phenylacetamido-3-[(triphenylphoranylidene)methyl]-3-cephem-4-carboxylate was added. The cooling bath was removed and the mixture vigorously stirred for 4 hours at 35° C. shaded from light under an N$_2$ atmosphere until complete dissolution of the phosphorane had occurred.

The resulting solution was vacuum concentrated and the residue was dissolved in 2 l of ethanol, and the solution was vacuum concentrated to a semi-crystallized residue which was slurried with 3 l of ethanol.

The mixture was stirred for 2 hours at +5° C. and let stand overnight, crystals were collected twice, washed with ethanol, and vacuum dried at room temperature. Yield 191 g (47%). M.p. 124°–128° C. contains 7.5% of trans isomer (determined by HPLC column Lichrosorb Si 60 5 μm Merck eluted with 85% toluene, 15% ethyl acetate).

PROCEDURE 2

Diphenylmethyl 7-Amino-3-(Z)-propen-1-yl)ceph-3-em-4-carboxylate Hydrochloride

To a stirred solution of 159.7 g (0.767 mole) of PCl$_5$ in 2.8 l CH$_2$Cl$_2$ were added 56.7 ml (0.700 mole) of pyridine in 280 ml CH$_2$Cl$_2$ over a 20 minute period. Under a nitrogen atmosphere the slurry was cooled to 2° C. while 256 g of the product of Procedure 1 (0.488 mole) was added. The mixture was stirred for 40 minutes and the resulting slurry was poured rapidly into a vigorously stirred solution of 1.4 l of CH$_2$Cl$_2$, and 209 ml (2.33 moles) of 1,3-butanediol at −20° C., so that the temperature did not rise above −5° C. The cooling bath was removed and after 45 minutes the temperature rose to 10° C. and was held there for 35 minutes. Water (1.0 liter) was added and stirring continued for 5 minutes after which the layers were allowed to separate. The organic layer was washed with 600 ml HCl 2N and then 400 ml saturated brine. The combined aqueous extracts were back-washed with 2×600 ml of CH$_2$Cl$_2$ and combined with the original CH$_2$Cl$_2$ extract.

The CH$_2$Cl$_2$ extract was dried over anhydrous MgSO$_4$. The MgSO$_4$ slurry was filtered and the MgSO$_4$ washed with 2×500 ml CH$_2$Cl$_2$. The combined filtrates were concentrated in vacuo on the rotary evaporator to a volume of 2.4 liters and diluted with 2.5 liters of ethyl acetate. The solution was concentrated again to a volume of ca. 1.3 liters. The resulting crystal-slurry was filtered, washed with 3×300 ml ethyl acetate. After air and vacuum drying over P$_2$O$_5$ there was obtained 149.8 g of the title compound as beige crystals. Yield 69.3%.

PROCEDURE 3

7-Amino-3-[(Z)-1-propen-1-yl]ceph-3-em-4-carboxylic Acid

To a stirred solution of 260 ml anisole and 1.38 l of trifluoroacetic acid (TFA) cooled to 0° C. was added 149.7 g (0.338 mole) of diphenylmethyl 7-amino-3-[(Z)-1-propen-1-yl]-3-cephem-4-carboxylic acid hydrochloride (0.338 mole, Procedure 2). The resulting slurry was then stirred at room temperature for 1 hour. Most excess of TFA was removed in vacuo on the rotary evaporator. The residual supernatant solution was decanted and the residual slurry was triturated with 1.5 l of dry ether during 1 hour. The crystalline product was filtered and dried over P$_2$O$_5$ to give 87.24 g of the trifluoroacetate of title compound. These 87.24 g of the trifluoroacetate were suspended and stirred into 900 ml of water (pH ca. 2.5). The mixture was cooled to +5° C. and then adjusted to pH 0.6 with 12N HCl. The yellow solution was charcoal treated and the slurry was filtered on a diatomaceous filter aid pad. The resulting solution was cooled to +5° C. and the pH was adjusted to 2.0 with 20% NaOH. The suspension was kept 1 hour in a refrigerator to aid crystallization. The crystals were collected, washed with 800 ml of water, 800 ml of acetone and vacuum dried at room temperature. Yield 69.4 g (85.5%). Contains 9.7% of trans isomer (determined by HPLC column RP 18 MERCK; H$_2$(NH$_4$)PO$_4$, 0.1 mole 95 ml+CH$_3$CN 5 ml; detected at 290 nm).

PROCEDURE 4

7-[(D)-2-Amino-2-(4-hydroxyphenyl)acetamido]-3-[(Z)-1-propenyl]ceph-3-em-4-carboxylic Acid 1.5 DMF Solvate

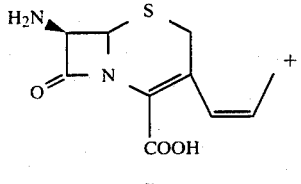

Ib

MW = 240.28

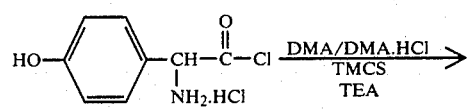

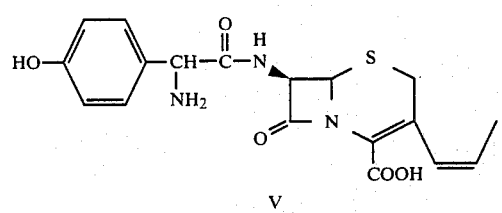

1.5 DMF Solvate, MW = 512

To a stirred slurry of 54 g (0.225 mole) of the product of Procedure 3 in 1.2 liter of CH$_2$Cl$_2$ were added 59.9 ml (0.472 mole) of trimethylchlorosilane, 28.9 ml (0.229 mole) of dimethylaniline and 62.64 ml (0.432 mole) of triethylamine keeping the temperature at 20° C. The resulting slurry was stirred for 2 hours at 20° C. and then cooled at −10° C. Dimethylanilin hydrochloride, 27.4 ml (33%), was added and then 64.3 g (0.229 mole) (80% estimated purity) of p-hydroxyphenylglycine chloride hydrochloride were added during 45 minutes in four portions. The slurry was stirred for 2 hours at −10° C., 23 ml of methanol were added and the mixture stirred 10 minutes. At that point 350 ml of water were added dropwise with a vigorous stirring (in order to avoid the formation of a gum). The mixture was cooled at +5° C. and the pH was adjusted to 2.2 with triethylamine. The aqueous phase (650 ml) was washed three times with 150 ml CH$_2$Cl$_2$. Insoluble material was filtered and the pH of aqueous phase was adjusted to 4.5 with triethylamine and dimethylformamide (1.3 liter) and isopropanol (0.65 l) were added. The mixture was stirred for 2 hours and let stand overnight at +5° C. Crystals were collected, washed with the minimum amount of dimethylformamide and then three times with 200 ml of acetone and vacuum dried at room temperature. Yield 74.4 g of 28100 as dimethylformamide solvate (=64%), having the composition corresponding to 1.5 moles of dimethylformamide per mole of 7[(D)-2-amino-2-(4-hydroxyphenyl)acetamido]-3-[(Z)-1- propenyl]ceph-3-em-4-carboxylic acid. This solvate is characterized by the following spectral data.

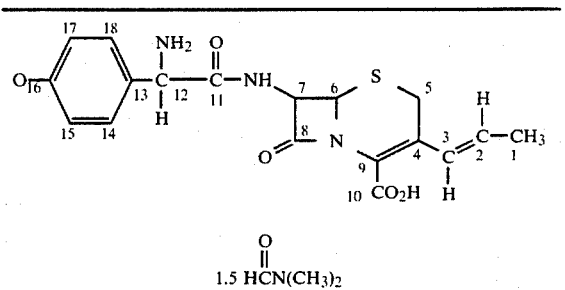

$$1.5 \; HCN(CH_3)_2$$

| $^1$H 360 MHz NMR (in D$_2$O/DCl solution) 1.5 DMF Solvate | | | |
|---|---|---|---|
| δ(ppm)* | Description | No. of Protons | Assignment |
| 7.92 | Singlet | 1.5 | $H\underline{C}-N$ (DMF) (O=) |
| 7.4 | Doublet | 2 | C$_{14}\underline{H}$, C$_{18}\underline{H}$ |
| 6.98 | Doublet | 2 | C$_{15}\underline{H}$, C$_{17}\underline{H}$ |
| 6.05 | Multiplet | 1 | C$_3\underline{H}$ |
| 5.75–5.9 | Multiplet | 1 | C$_2\underline{H}$ |
| 5.72 | Doublet | 1 | C$_7\underline{H}$ |
| 5.18 | Doublet | 1 | C$_6\underline{H}$ |
| 5.16 | Singlet | 1 | C$_{12}\underline{H}$ |
| 3.25–3.55 | Multiplet | 2 | C$_5\underline{H}_2$ |
| 3.0 | Singlet | 4.5 | NC$\underline{H}_3$ (DMF) |
| 2.86 | Singlet | 4.5 | NC$\underline{H}_3$ (DMF) |
| 1.60 | Singlet | 3 | C$_1\underline{H}_3$ |

*TSP as reference

| IR (KBr pellet) (see FIG. 1) 1.5 DMF Solvate | |
|---|---|
| Wave Number (cm$^{-1}$) | Functional Group |
| 2600–3250 | OH, NH, NH$_3^+$ |
| 1780 | β-lactam C=O |
| 1700 | Amide C=O |
| 1665 | Amide C=O (DMF) |
| 1570 | CO$_2^-$ |
| 1400 | CO$_2^-$ |

| X-ray Powder Diffraction* 1.5 DMF Solvate | | | |
|---|---|---|---|
| d (Å) | I/Io | d (Å) | I/Io |
| 13.24 | 100 | 4.39 | 25 |
| 9.50 | 8 | 4.29 | 33 |
| 7.82 | 9 | 4.10 | 13 |
| 7.42 | 10 | 4.04 | 10 |
| 7.14 | 12 | 3.69 | 5 |
| 6.76 | 15 | 3.62 | 6 |
| 5.88 | 5 | 3.58 | 9 |
| 5.28 | 10 | 3.56 | 8 |
| 5.06 | 3 | 3.48 | 4 |
| 4.82 | 10 | 3.29 | 10 |
| 4.72 | 8 | 3.19 | 5 |
| 4.64 | 5 | 2.98 | 5 |
| 4.53 | 9 | 2.71 | 4 |
| 4.47 | 16 | | |

*Determined on a Rigaku Powder Diffractometer using a copper target X-ray tube, a nickel filter, and the sample contained in a glass dish. The scan rate was 2° per minute over the range from 5° to 40°, and a chart was mechanically recorded to show the angles of maximum diffraction. From this the (d) spacings and relative intensities (I/I°) were calculated.

PROCEDURE 5

7-[(D)-2-Amino-2-(4-hydroxyphenyl)acetamido]-3-[(Z)-1-propenyl]ceph-3-em-4-carboxylic Acid The dimethylformamide solvate from Procedure 4, 25 g, was dissolved in 400 ml H$_2$O. After filtration of insoluble material the solution was injected on a 80 mm diameter column (MODULPREP, JOBIN-YVON) filled with the Lichroprep and chromatographed with the solvent system H$_2$O-acetonitrile 92-8. Detection of the product was monitored at 325 nm and controlled by analytical HPLC. The appropriate fractions (10 to 20) were, collected (each fraction of ca 250 ml) and concentrated to 1.5 l (to eliminate acetonitrile), this solution was frozen at −60° C. and lyophilized. The lyophilized pad (14.2 g) was poured into 140 ml of water and stirred 10 minutes in an ice-bath. The resulting crystalline product was collected and dried under vacuum (without P$_2$O$_5$) during one night. There was obtained 13.34 g of the title compound, purification yield 65%.

What is claimed is:

1. The crystalline dimethylformamide solvate of 7-[(D)-2-amino-2-(4-hydroxyphenyl)acetamido]-3-((Z)-1-propen-1-yl)-3-cephem-4-carboxylic acid having the composition corresponding to the formula C$_{18}$H$_{19}$N$_3$O$_5$S.(C$_3$H$_7$NO)$_{1.5}$ and the following X-ray powder diffraction pattern.

| d(Å) | I/Io |
|---|---|
| 13.24 | 100 |
| 9.50 | 8 |
| 7.82 | 9 |
| 7.42 | 10 |
| 7.14 | 12 |
| 6.76 | 15 |
| 5.88 | 5 |
| 5.28 | 10 |
| 5.06 | 3 |
| 4.82 | 10 |
| 4.72 | 8 |
| 4.64 | 5 |
| 4.53 | 9 |
| 4.47 | 16 |
| 4.39 | 25 |
| 4.29 | 33 |
| 4.10 | 13 |
| 4.04 | 10 |
| 3.69 | 5 |
| 3.62 | 6 |
| 3.58 | 9 |
| 3.56 | 8 |
| 3.48 | 4 |
| 3.29 | 10 |
| 3.19 | 5 |
| 2.98 | 5 |
| 2.71 | 4. |

2. The process of preparing the dimethylformamide solvate of claim 1 which comprises contacting 7-[(D)-2-amino-2-(4-hydroxyphenyl)acetamido]-3-((Z)-1-propen-1-yl)-3-cephem-4-carboxylic acid with at least 1.5 molecular proportions of dimethylformamide in an inert liquid medium in which said solvate is insoluble.

3. The process of claim 2 wherein said liquid medium comprises dimethylformamide, methanol, or water.

4. The method of claim 2 wherein an aqueous solution of 7-[(D)-2-amino-2-(4-hydroxyphenyl)acetamido]-3-((Z)-1-propen-1-yl)-3-cephem-4-carboxylic acid is treated with dimethylformamide at pH 4.5.

* * * * *